US00PP33412P2

(12) United States Plant Patent
Davasse

(10) Patent No.: US PP33,412 P2
(45) Date of Patent: Aug. 31, 2021

(54) ***HYDRANGEA* PLANT NAMED 'JPD01'**

(50) Latin Name: ***Hydrangea macrophylla* x *Hydrangea serrata***
Varietal Denomination: JPD01

(71) Applicant: Curoplant Company Ltd., Abbotsford (CA)

(72) Inventor: Jean-Paul Davasse, Angers (FR)

(73) Assignee: CUROPLANT COMPANY LTD., Abbotsford (CA)

( * ) Notice: Subject to any disclaimer, the term of this patent is extended or adjusted under 35 U.S.C. 154(b) by 0 days.

(21) Appl. No.: 17/062,366

(22) Filed: Oct. 2, 2020

(30) Foreign Application Priority Data

Jun. 29, 2020 (CA) ..... PBR 20-10276

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02
See application file for complete search history.

(56) References Cited

PUBLICATIONS

PLUTO UPOVROM Plant Variety Database 20210312 Citation for 'JPD01' as per QZ PBR 20190264; Apr. 16, 2019; 1 page.*

* cited by examiner

*Primary Examiner* — Kent L Bell
(74) *Attorney, Agent, or Firm* — Penny J. Aguirre

(57) ABSTRACT

A new cultivar of *Hydrangea* hybrid plant named 'JPD01' that is characterized by its leaves that are dark in color and fade to dark red in autumn, becoming more black in color in acidic soil and more red in color in neutral soil, its blooms on terminal, lateral and basal buds with a period of flowering that begins in mid-June, its lacecap inflorescences that are pink-red in color turning dark red in color in autumn until frost, its dried flowers that stay dark red in color in a vase for more than a year, its compact plant habit that is well-branched with rigid stems, and its good cold hardiness and is not affected by the frost in spring as it blooms on basal and lateral buds.

2 Drawing Sheets

Botanical classification: *Hydrangea macrophylla* x *Hydrangea serrata.*

Varietal denomination: 'JPD01'.

CROSS REFERENCE TO A RELATED APPLICATIONS

This application is related to a European plant breeders' rights application filed on Jan. 28, 2019, application No. 2019/0264 and a Canadian plant breeders' rights application filed Jun. 29, 2020 application No. 20-10276. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Hydrangea macrophylla* x *Hydrangea serrata* named 'JPD01' and will be referred to hereafter by its cultivar name, 'JPD01'. 'JPD01' represents a new *Hydrangea*, a perennial shrub grown for landscape use and as a potted plant.

'JPD01' was derived from an ongoing controlled breeding program directed by the Inventor. An objective of the breeding program included developing a new cultivar of

*Hydrangea* with dark leaves, attractive fall foliage and flower colors that is free flowering and hardy.

'JPD01' arose from a controlled cross made by the Inventor in Angers, France in June of 2013 between *Hydrangea* 'Julisa' (not patented) as the female parent and *Hydrangea* 'MAK20' (U.S. Plant Pat. No. 24,820) as the male parent. 'JPD01' was selected as a single unique plant from amongst the resulting seedlings in May of 2014 in Sainte Gemmes sur Loire, France.

Asexual propagation of the new cultivar was first accomplished by stem cuttings by the Inventor in July of 2014 in Sainte Gemmes sur Loire, France. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'JPD01' as a unique cultivar of *Hydrangea.*

1. 'JPD01' exhibits leaves that are dark in color and fade to dark red in autumn, leaves become more black in color in acidic soil and more red in color in neutral soil.
2. 'JPD01' exhibits blooms on terminal, lateral and basal buds with a period of flowering that begins in mid-June.

3. 'JPD01' exhibits lacecap inflorescences that are pink-red in color turning dark red in color in autumn until frost.
4. 'JPD01' exhibits dried flowers that stay dark red in color in a vase for more than a year.
5. 'JPD01' exhibits a compact plant habit that is well-branched with rigid stems.
6. 'JPD01' exhibits good cold hardiness and is not affected by the frost in spring as it blooms on basal and lateral buds.

'Julisa', the female parent of 'JPD01', differs from 'JPD01' in having mophead type inflorescences that are blood red in color when blooms are opening. 'MAK20', the male parent, differs from 'JPD01' in having stems that are less rigid and yellow-green in color with dark lenticels; the stems of 'JPD01' are green and tinged with red in late summer and fall. 'JPD01' can be most closely compared to the *Hydrangea macrophylla* cultivar 'Dark Angel' (not patented) and *Hydrangea serrata* 'Spreading Beauty' (not patented). 'Dark Angel' is similar to 'JPD01' in having dark foliage and flowers that are red-pink in color. 'Dark Angel' differs from 'JPD01' in having leaves that are lighter in color with veins that are more green and inflorescences that are lighter in color and a different form. 'Spreading Beauty' is similar to 'JPD01' in having sepals that are similar in shape. 'Spreading Beauty' differs from 'JPD01' in having leaves that are lighter in color, flowers that are lighter red in color and a less upright plant habit.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Disclosures include but may not be limited by a description at the Chantilly Plant Show and website listings by New Plants, Norfolk Quality Plants, Gardening Express Company, Boos Hortensia, Twitter, and Facebook.

BRIEF DESCRIPTION OF THE DRAWINGS

The accompanying colored photographs illustrate the overall appearance and distinct characteristics of the new *Hydrangea*. The photographs were taken of an 18-month-old plant of 'JPD01' as grown in a cold greenhouse in a 2-gallon container in in Abbotsford, B.C. Canada.

The photograph in FIG. 1 provides a side view of the plant habit of 'JPD01' in bloom.

Figure 1:
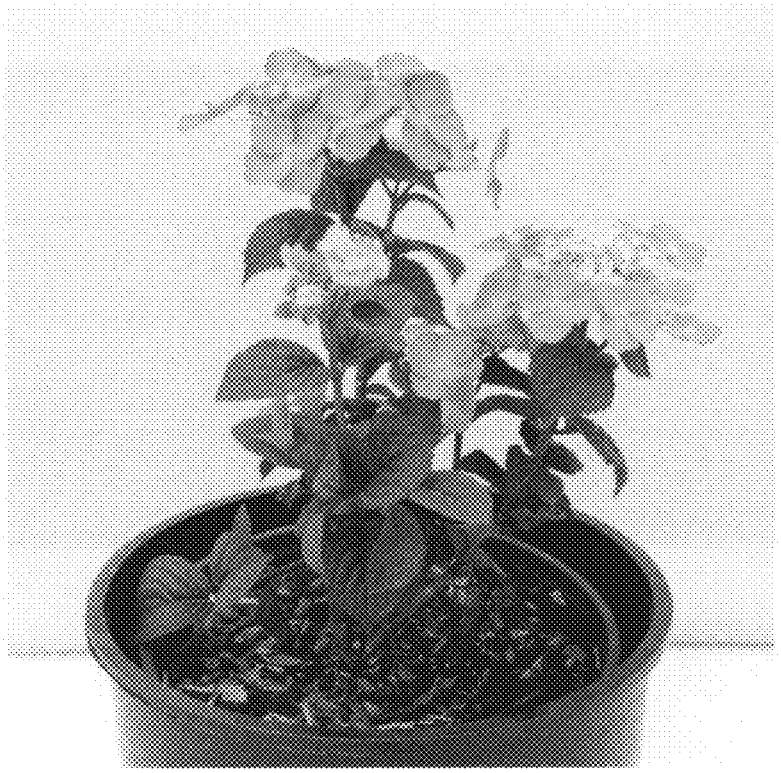
Figure 2:
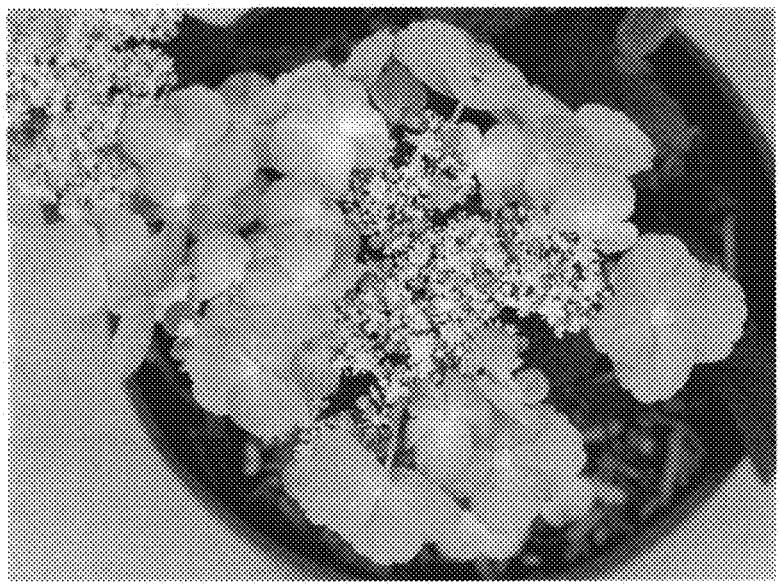

The photograph in FIG. 2 provides a close-up view of a fully open inflorescence of 'JPD01'.

Figure 3:
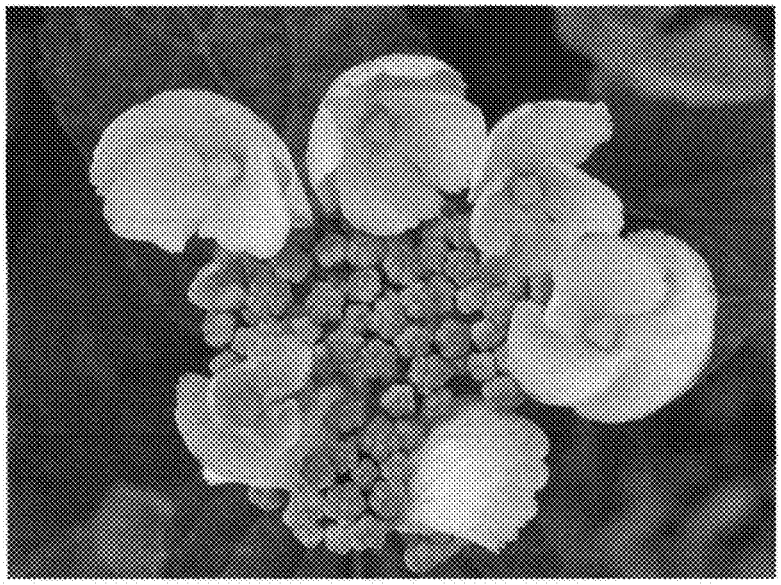

The photograph in FIG. 3 provides a close-up view of the opening flowers and flower buds of 'JPD01'.

Figure 4:
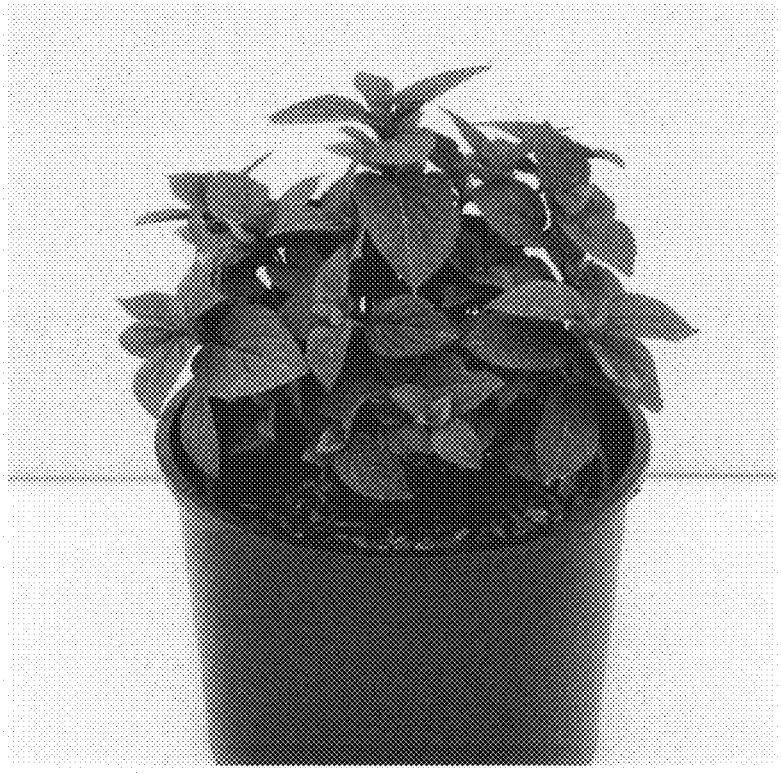

The photograph in FIG. 4 provides a close-up view of the foliage of 'JPD01'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of 18-month-old plants of 'JPD01' as grown in a cold greenhouse in 2-gallon containers in in Abbotsford, B.C., Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Begins in mid-June and remains showy into fall as they turn color.

*Plant type*.—Deciduous shrub.

*Plant habit*.—Compact, upright-bushy, overall globular in shape.

*Height and spread*.—Average 26 cm in height and 25.3 cm in diameter.

*Hardiness*.—At least in U.S.D.A. Zones 5 to 9.

*Diseases and pests*.—No susceptibility or resistance to diseases or pests has been observed.

*Root description*.—Fibrous, dense, moderately branched.

*Propagation*.—Softwood stem cuttings.

*Growth rate and vigor*.—Slow to moderate.

Stem description:

*Stem shape*.—Round, weakly ribbed.

*Stem strength*.—Strong.

*Stem aspect*.—Upright to an average angle of 70°.

*Stem color*.—Immature stem; 146C with N77A at nodes, lenticels 183C, mature stem; 199C to 199D and 156A and flushed with 183B late summer and fall.

*Stem size*.—Average of 22.5 cm in length (excluding the inflorescence) and 5.8 mm in diameter.

*Stem surface*.—Weak glossiness, very sparse pubescence.

*Branching*.—Dense, freely branching, with an average of 4 lateral branches.

*Internode length*.—Average of 7.6 cm.

Foliage description:

*Leaf shape*.—Ovate.

*Leaf arrangement*.—Opposite.

*Leaf division*.—Simple.

*Leaf number*.—Average of 8 (4 pairs) per lateral branch.

*Leaf base*.—Obtuse.

*Leaf apex*.—Acute, apiculate.

*Leaf margins*.—Serrated.

*Leaf venation*.—Pinnate, upper surface; 145C and 181B to 181B, lower surface; 147C lightly streaked with 185C.

*Leaf size*.—Average of 6.5 cm in length and 4.9 cm in width.

*Leaf attachment*.—Petiolate.

*Leaf surface*.—Upper and lower surface; smooth and moderately rugose.

*Leaf color*.—Immature upper surface; between 144A to 144B with 178A along margin edge, immature lower surface; 146C, mature upper surface; closest to 147A tinged with N77A with age, mature lower surface; 147B, fall upper surface; N77A with hues of 187A to 187B, fall lower surface; 148C tinged with 182B to 182C.

*Petioles*.—Average of 0.8 cm in length and 3.0 mm in diameter, upper surface color mature and fall; 187A, lower surface color; 148C strongly tinged with 183C, 183B in fall, upper and lower surfaces are smooth and glossy.

Inflorescence description:

*Inflorescence type*.—Flattened, compound corymb of single sterile and fertile flowers.

*Lastingness of inflorescence*.—Sterile flowers; persistent, lasting about 6 weeks, fertile flowers; self-cleaning, lasting about 1 week.

*Inflorescence number*.—One per lateral or sublateral stem.

*Inflorescence size*.—Average of 4.6 cm in height and 10.1 cm in diameter.

*Flower number*.—An average of 9 sterile flowers and 108 fertile flowers per inflorescence.

*Flower fragrance*.—None.

*Flower aspect*.—Sterile flowers; upright to outward and slightly drooping, fertile flowers; upright.

*Flower size*.—Sterile flowers; rotate in shape, average of 3.8 cm in diameter and 1.9 cm in depth, fertile flowers; rotate, average of 7 mm in diameter and 4 mm in depth.

*Flower buds*.—Sterile flowers; average of 7 mm in length and 4 mm in diameter, ovate in shape and 145A in color, fertile flowers; average of 3 mm in length and 3.5 mm in diameter, oblate in shape, immature 145C, before opening N57C to N57D, base N155B in color.

*Peduncles*.—Average of 2.7 cm in length and 3 mm in width, strong, 148A in color, surface is moderately pubescent, lenticels average of 4 per cm, 3 mm in length and 1 mm in width and 181B in color.

*Pedicels*.—Sterile Flowers; average of 1.2 cm in length and 2 mm in diameter, held at an average angle of 30°, strong, 65B in color, surface is densely covered with thin hairs; average of 0.5 mm in length and NN155B in color, fertile flowers; average of 5 mm in length and 1 mm in diameter, at an average angle of 10°, moderate in strength, 185D in color, surface is sparsely covered with dull pubescent short thin hairs; average of 0.5 mm in length and NN155B in color.

*Petals*.—Sterile flowers; average of 4 in a rotate arrangement, elliptic and concave in shape, acute apex, cuneate base, entire margin, average of 3 mm in length and 2 mm in width, upper and lower surfaces glabrous, color: upper surface before opening; 150D, and fully open; NN155A tinged lightly with 65A, lower surface before opening and fully open; N155B, not fading, but dropped when mature, fertile flowers; average of 5 in a rotate arrangement, elliptic to ovate, and concave in shape, acute apex, cuneate base, entire margin, average of 2 mm in length and 1 mm in width, upper and lower surface texture is smooth and dull, color: upper surface and lower surface before opening; 145C, upper surface when fully opened; 62A to 62B, lower surface when fully opened; 61B to 61C and NN155C at base.

*Sepals*.—Sterile flowers; average of 4, rotate in arrangement, moderately overlapping margins, both surfaces smooth and matte, depressed (very shallow) ovate in shape, margin is crenate, bluntly obtuse apex, truncate base, an average of 2.7 cm in length and 1.9 cm in width, color: upper surface when opening; N57D, base N155D, lower surface when opening; 65A, base N155D, upper surface when fully open; N57C to N57D, lower surface when fully open; 65A with tinges of N57C to N57D, fading to upper side in fall; closest to 185B to 185D, fading to lower side in fall; 185C to 185D with tinges of 161C, fertile flowers; average of 5 petals in a rotate arrangement, elliptic to ovate, and concave in shape, acute apex, cuneate base, entire margin, average of 2 mm in length and 1 mm in width, upper and lower surface texture is smooth and dull, color: upper surface and lower surface before opening; 145C, upper surface when fully opened; 62A to 62B, lower surface when fully opened; 61B to 61C and NN155C at base.

Reproductive organs:

*Androecium*.—Sterile flowers; stamens; average of 8, filaments; average of 2.5 mm in length and 157D in color, anthers; broad kidney-shaped, 1.0 mm in length and 155A in color, pollen; low in quantity and 158D in color, fertile flowers; stamens; average of 8, filaments; average of 3.5 mm in length and 157D in color, anthers; broad kidney-shaped, less than 1.0 mm in length and 155A in color, pollen; moderate in quantity and 158D in color.

*Gynoecium*.—Sterile flowers; pistils; average of 3, 2.5 mm in length, stigma; club-shaped and 157A in color, style; 1.0 mm in length and 158D in color, ovary; 144C to 144D in color, fertile flowers; pistils; average of 3, 2 mm in length, stigma; club- shaped and 157A in color, style; 0.5 mm in length and 157D in color, ovary; 145B to 145C in color.

*Fruit and seed*.—No seeds or fruit observed to date.

It is claimed:

1. A new and distinct cultivar of *Hydrangea* plant named 'JPD01' substantially as herein illustrated and described.

* * * * *